US008334291B2

(12) United States Patent
Schirok et al.

(10) Patent No.: US 8,334,291 B2
(45) Date of Patent: Dec. 18, 2012

(54) ALIPHATICALLY SUBSTITUTED PYRAZOLOPYRIDINES, AND THE USE THEREOF

(75) Inventors: Hartmut Schirok, Langenfeld (DE); Nils Griebenow, Dormagen (DE); Chantal Fürstner, Mülheim/Ruh (DE); Joachim Mittendorf, Wuppertal (DE); Johannes-Peter Stasch, Solingen (DE); Frank Wunder, Wuppertal (DE); Stefan Heitmeier, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/133,383

(22) PCT Filed: Dec. 8, 2009

(86) PCT No.: PCT/EP2009/008741
§ 371 (c)(1),
(2), (4) Date: Jun. 7, 2011

(87) PCT Pub. No.: WO2010/078900
PCT Pub. Date: Jul. 15, 2010

(65) Prior Publication Data
US 2011/0245273 A1 Oct. 6, 2011

(30) Foreign Application Priority Data

Dec. 19, 2008 (DE) .................. 10 2008 063 992

(51) Int. Cl.
*A01N 43/54* (2006.01)
*C07D 239/42* (2006.01)
*C07D 401/04* (2006.01)

(52) U.S. Cl. .................. 514/256; 544/296; 546/275.7; 546/117; 546/119

(58) Field of Classification Search .................. 544/296; 514/256; 546/275.7, 117, 119
See application file for complete search history.

(56) References Cited

U.S. PATENT DOCUMENTS

| 5,994,378 | A | 11/1999 | Matsuo et al. |
| 6,166,027 | A | 12/2000 | Straub et al. |
| 6,180,656 | B1 | 1/2001 | Furstner et al. |
| 6,362,178 | B1 | 3/2002 | Niewohner et al. |
| 6,451,805 | B1 | 9/2002 | Straub et al. |
| 6,693,102 | B2 | 2/2004 | Stasch et al. |
| 6,743,798 | B1 | 6/2004 | Straub et al. |
| 6,833,364 | B1 | 12/2004 | Straub et al. |
| 6,903,089 | B1 | 6/2005 | Stasch et al. |
| 7,105,523 | B2 | 9/2006 | Stasch et al. |
| 7,173,037 | B2* | 2/2007 | Alonso-Alija et al. ....... 514/256 |
| 7,427,617 | B2 | 9/2008 | Feurer et al. |
| 7,514,463 | B2 | 4/2009 | Georg et al. |
| 2004/0067937 | A1 | 4/2004 | Stasch et al. |
| 2004/0171832 | A1 | 9/2004 | Stasch et al. |
| 2004/0235863 | A1 | 11/2004 | Feurer et al. |
| 2005/0222170 | A1 | 10/2005 | Welgand et al. |
| 2006/0052397 | A1 | 3/2006 | Alonso-Alija et al. |
| 2007/0225299 | A1 | 9/2007 | Bischoff et al. |
| 2010/0029653 | A1 | 2/2010 | Schirok et al. |
| 2010/0113507 | A1 | 5/2010 | Furstner et al. |
| 2012/0022084 | A1* | 1/2012 | Follmann et al. .......... 514/256 |

FOREIGN PATENT DOCUMENTS

| CA | 2346698 A1 | 4/2000 |
| CA | 2577420 | 3/2006 |
| CA | 2272584 A1 | 10/2007 |
| CA | 2749048 A1 | 7/2010 |
| EP | 0463756 B1 | 4/1995 |
| WO | 9428902 A1 | 12/1994 |
| WO | 9519978 A1 | 7/1995 |
| WO | 0006567 A1 | 2/2000 |
| WO | 0157024 A1 | 8/2001 |
| WO | 03035005 A2 | 5/2003 |
| WO | 03076408 | 9/2003 |
| WO | WO 03095451 A1 * | 11/2003 |
| WO | 2004031187 A1 | 4/2004 |
| WO | 2005030121 A2 | 4/2005 |
| WO | 2005044816 A1 | 5/2005 |
| WO | 2005080391 | 9/2005 |

OTHER PUBLICATIONS

U.S. Appl. No. 12/299,906, filed May 18, 2009.
U.S. Appl. No. 12/441,242, filed Mar. 13, 2009.
U.S. Appl. No. 13/143,415, filed Sep. 16, 2011.
Mittendorf et al., "Discovery of Riociguat (BAY 63-2521): A Potent, Oral Stimulator of Soluble Guanylate Cyclase for the Treatment of Pulmonary Hypertension," Chem Med Chem, 2009, No. 4, 853-865.
Ko et al., "YC-1, a Novel Activator of Platelet Guanylate Cyclase;" Blood, 1994, 84, pp. 4226-4233.
Mülsch et al., "Effect of YC-1, an NO-independent, Superoxide-Sensitive Stimulaotr of Soluble Gyanylyl Cyclase, on Smooth Muscle Responsiveness to Nitrovasodilators;" Brit. J. Pharm., 1997, 120, pp. 681-689.
Goldberg et al., "Stimulation of Human Platelet Guanylate Cyclase by Fatty Acids," J. Biol. Chem., 1977, 252, pp. 1279-1285.
Pettibone et al., "A Structurally Novel Stimulator of Guanylate Cyclase with Long-Lasting Hypotensive Activity in the Dog," Euro. J. of Pharmacology, 1985, 116, pp. 307-312.

(Continued)

*Primary Examiner* — James O Wilson
*Assistant Examiner* — Alexander R Pagano
(74) *Attorney, Agent, or Firm* — Karen B. King

(57) ABSTRACT

The present application relates to novel aliphatically substituted pyrazolopyridines, to processes for their preparation, to their use, alone or in combination, for the treatment and/or prevention of diseases and to their use for preparing medicaments for the treatment and/or prevention of diseases, in particular for the treatment and/or prevention of cardiovascular disorders.

5 Claims, No Drawings

OTHER PUBLICATIONS

Yu et al., "Vasorelaxant Effect of Isoliquiritigenin, A Novel Soluble Guanylate Cyclase Activator, in Rat Aorta," Brit. J. of Pharmacology, 1995, 114, pp. 1587-1594.

Cavalieri et al., "A Synthesis of Adenine: The Incorporation of Isotopes of Nitrogen and Carbon," J. Am. Chem. Soc.,1949, 71, pp. 533-536.

Barraclough et al., "Mono-aroylation of 2,3-and 3,4-Diaminopyridine and 4,5-Diaminopyrimidine, and Syntheses of Putative Inotrope/b-Adrenoceptor Antagonists," J. Chem. Res., 1996, vol. 9, 2316-2335.

Li et al., "Synthesis and Structure-Activity Relationships of 2-Pyridones: A Novel Series of Potent DNA Gyrase Inhibitors as Antibacterial Agents," J. Med. Chem. 1996, 39, pp. 3070-3088.

Evans et al. "The Preparation of 4-Amino-and Other Pteridines," J. of Chem. Soc. 1956, pp. 4106-4113.

Schwoch et al. "2-3-Dihydrospirol [1H-4 and 5-azabenzimidazole-2,1'-cyclohexane](=Spiro[cyclohexane-1.2'(3'H)-imidaxo[4,5-hb]pyridine] and Spiro[cyclohexane-1.2"(3"H)-1"H-imidaxo[4,5-c[pyridine]): Reactions with Nucleophiles," Helvetia Chimica Acta, 1994, vol. 77, pp. 2175-2190.

Wu et al., "YC-inhibited human platelet aggregation through NO-independent activation of soluble guanylate cyclase," Br. J. Pharmacol., Oct. 1995, 116(3): 1973-1978.

An English equivalent of WO 2000/0657, as filed at US national stage, U.S. Appl. No. 09/744,704 (unpublished).

Kim et al., "Cirsium japonicum elicits endothelium-dependent relaxation via histamine H1-receptor in rat thoracic aorta," Journal of Ethnoparmacology, 2008, vol. 116, 223-227.

Corsi et al, "1-Halobanzyl-1H-indazole 3-carboxlic acids. A new class of antispermatogenic agents," Journal of Medicinal Chemistry, 1976, 19(6), 778-83.

Powers-Martin et al., Immunothistochemical assessment of cyclic tuanosine monophosphate (cGMP) and soluble guanylate cyclase (sGC) within the rostral ventrolateral medula, J. Biomed Sci., 2008, 150, pp. 801-812.

Zhao et al., "Effect of aspirin, clopidogrel and dipyridamole on soluble markers of vascular function in normal volunteers and patients with prior ischameic stroke," Platelets, 2006, 17(2), pp. 100-104.

Glass, D.B., et al., "Stimulation of Human Platelet Guanylate Cyclase by Fatty Acids," J. Bio. Chem., 1977, vol. 232, No. 4, Feb. 25, pp. 1279-1285.

Hajos, et al., "Product Class 5: Azaindolizines with two nitrogen atoms in the five-membered ring," Science of Synthesis, 2002, vol. 12, pp. 613-678 Georg Thieme Verlag, Stuttgart, New York.

Palacios et al. "A new and efficient synthesis of imidazo[1,5]pyridine derivatives by a tandem Aza-Wittig/electocyclic ring closure of N-vinylic phosphazenes," Tetrahedron, 1995, vol. 51, No. 12, pp. 3683-3690, Elsevier Science Ltd., United Kingdom.

* cited by examiner

ALIPHATICALLY SUBSTITUTED PYRAZOLOPYRIDINES, AND THE USE THEREOF

This application is the National Stage of International Patent Application No. PCT/EP2009/008741, filed Dec. 8, 2009, which claims the benefit of priority of German Patent Application No. DE 10 2008 063 992.3, filed Dec. 19, 2008.

The present application relates to novel aliphatically substituted pyrazolopyridines, to processes for their preparation, to their use, alone or in combination, for the treatment and/or prevention of diseases and to their use for preparing medicaments for the treatment and/or prevention of diseases, in particular for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. Carbon monoxide (CO) is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, myocardial infarction, thromboses, stroke and sexual dysfunction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole [YC-1, Wu et al., *Blood* 84 (1994), 4226; Müilsch et al., *Brit. J. Pharmacol.* 120 (1997), 681], fatty acids [Goldberg et al., *J. Biol. Chem.* 252 (1977), 1279], diphenyliodonium hexafluorophosphate [Pettibone et al., *Eur. J. Pharmacol.* 116 (1985), 307], isoliquiritigenin [Yu et al., *Brit. J. Pharmacol.* 114 (1995), 1587] and various substituted pyrazole derivatives (WO 98/16223).

Fused pyrazole derivatives are described inter alia in WO 98/23619, WO 00/06568, WO 00/06569, WO 02/42299, WO 02/42300, WO 02/42301, WO 02/42302, WO 02/092596, WO 03/004503, WO 03/095451, WO 2007/124854, WO 2007/128454 and WO 2008/031513 as stimulators of soluble guanylate cyclase. However, it was found that some of these compounds have disadvantages with respect to their physicochemical properties such as, for example, their solubility, or with respect to their in vivo properties such as, for example, their behavior in the liver, their pharmackokinetic behavior, their dose/activity relationship and/or their metabolic path.

Furthermore, WO 01/57024, WO 03/035005 and WO 2005/030121 disclose various fused pyrazole derivatives for treating disorders.

It was an object of the present invention to provide novel substances which act as stimulators of soluble guanylate cyclase and, compared to the compounds known from the prior art, have an identical or improved physicochemical, pharmacokinetic and/or therapeutic profile.

The present invention provides compounds of the general formula (I)

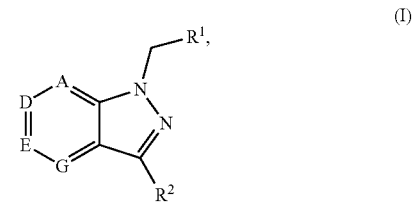

in which
A represents $CR^3$ or N,
  where
    $R^3$ represents hydrogen, halogen, cyano, $(C_1-C_4)$-alkyl, trifluoromethyl, amino, $(C_1-C_4)$-alkoxy or trifluoromethoxy,
D represents $CR^4$ or N,
  where
    $R^4$ represents hydrogen, halogen, cyano, $(C_1-C_4)$-alkyl, trifluoromethyl, amino, $(C_1-C_4)$-alkoxy or trifluoromethoxy,
E represents $CR^5$ or N,
  where
    $R^5$ represents hydrogen, halogen, cyano, $(C_1-C_4)$-alkyl, trifluoromethyl, amino, $(C_1-C_4)$-alkoxy or trifluoromethoxy,
G represents $CR^6$ or N,
  where
    $R^6$ represents hydrogen, halogen, cyano, $(C_1-C_4)$-alkyl, trifluoromethyl, amino, $(C_1-C_4)$-alkoxy or trifluoromethoxy,
with the proviso that at most 2 of the groups A, D, E and G represent N,
$R^1$ represents $(C_3-C_8)$-cycloalkyl,
  where $(C_3-C_8)$-cycloalkyl may be substituted by 1 or 2 substituents independently of one another selected from the group consisting of fluorine and $(C_1-C_4)$-alkyl,
$R^2$ represents pyrrolinyl, dihydropyrazolyl, imidazolinyl, dihydrooxazolyl, dihydroisoxazolyl, dihydro-1,2,4-triazolyl, dihydro-1,2,4-oxadiazolyl, dihydro-1,3,4-oxadiazolyl, dihydro-1,2,4-thiadiazolyl, dihydropyranyl, 1,4-dihydropyridyl, tetrahydropyrimidinyl, 1,3-oxazinyl, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl or triazinyl, where pyrrolinyl, dihydropyrazolyl, imidazolinyl, dihydrooxazolyl, dihydroisoxazolyl, dihydro-1,2,4-triazolyl, dihydro-1,2,4-oxadiazolyl, dihydro-1,3,4-oxadiazolyl, dihydro-1,2,4-thiadiazolyl, dihydropyranyl, 1,4-dihydropyridyl, tetrahydropyrimidinyl, 1,3-oxazinyl, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl and triazinyl may be substituted by 1 to 4 substituents independently of one another selected from the group consisting of halogen, azido, nitro, cyano, —$R^7$, —C(=O)—$R^7$, —C(=O)—$OR^7$, —C(=O)—$NR^7R^8$, —O—(C=O)$_n$—$R^7$, —O—C(=O)—$OR^7$, —O—C(=O)—$NR^7R^8$, —S(O)$_p$—$R^7$, —$SO_2$—$OR^7$, —$SO_2$—$NR^7R^8$, —$NR^7$—(C=O)$_n$—$R^8$, —$NR^7$—$SO_2$—$R^8$, —$NR^7$—C(=O)—$OR^8$, —$NR^9$—C(=O)—$NR^7R^8$ and —$NR^9$—$SO_2$—$NR^7R^8$, in which n represents a number 0 or 1, P represents a number 0, 1 or 2, $R^7$, $R^8$ and $R^9$ each independently of one another represent hydrogen, ($C_1$-$C_6$)-alkyl, ($C_2$-$C_6$)-alkenyl, ($C_3$-$C_8$)-cycloalkyl, ($C_3$-$C_8$)-cycloalkenyl, ($C_6$-$C_{10}$)-aryl, 4- to 8-membered heterocyclyl or 5- to 10-membered heteroaryl, in which $R^7$, $R^8$ and $R^9$ for their part may be substituted by 1 to 5 substituents independently of one another selected from the group consisting of halogen, azido, nitro, cyano, trifluoromethyl, ($C_1$-$C_6$)-alkyl, ($C_1$-$C_6$)-alkylcarbonyl, ($C_1$-$C_6$)-alkylcarbonyloxy, hydroxy-carbonyl, ($C_1$-$C_6$)-alkoxycarbonyl, aminocarbonyl, mono-($C_1$-$C_6$)-alkylaminocarbonyl, di-($C_1$-$C_6$)-alkylaminocarbonyl, hydroxyl, trifluoromethoxy, ($C_1$-$C_6$)-alkoxy, oxo, mercapto, ($C_1$-$C_6$)-alkylthio, amino, mono-($C_1$-$C_6$)-alkylamino, di-($C_1$-$C_6$)-alkylamino, formylamino, ($C_1$-$C_6$)-alkylcarbonylamino, ($C_1$-$C_6$)-alkoxy-carbonylamino, ($C_3$-$C_8$)-cycloalkyl, ($C_3$-$C_8$)-cycloalkenyl and 4- to 8-membered heterocyclyl, or $R^7$ and $R^8$ together with the radical to which the two are attached form a 4- to 8-membered heterocycle, or $R^7$ and $R^9$ together with the radical to which the two are attached form a 4- to 8-membered heterocycle, and N-oxides, salts, solvates, salts of N-oxides and solvates of N-oxides or salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

N-oxides of the compounds of the formula (I) and their salts, solvates and solvates of the salts are likewise compounds according to the invention.

The compounds according to the invention may, depending on their structure, exist in stereoisomeric forms (enantiomers, diastereomers). The present invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

In the context of the invention, alkyl represents a straight-chain or branched alkyl radical having the respective stated number of carbon atoms. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

In the context of the invention, cycloalkyl represents a monocyclic saturated alkyl radical having 3 to 8 carbon atoms. The following may be mentioned by way of example and by way of preference: cyclopropyl, cyclobutyl, cyclopentyl, cyclohexyl, cycloheptyl and cyclooctyl.

In the context of the invention, alkenyl represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

In the context of the invention, cycloalkenyl represents a monocyclic carbocycle having 3 to 8 carbon atoms and one double bond. The following may be mentioned by way of example and by way of preference: cyclobutenyl, cyclopentenyl, cyclohexenyl, cycloheptenyl and cyclooctenyl.

In the context of the invention, alkylcarbonyl represents a straight-chain or branched alkyl radical having 1 to 6 or 1 to 4 carbon atoms in the alkyl chain and a carbonyl group attached in the 1-position. The following may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

In the context of the invention, alkylcarbonyloxy represents a straight-chain or branched alkyl-carbonyl radical which is attached via an oxygen atom and which carries 1 to 6 or 1 to 4 carbon atoms in the alkyl chain. The following may be mentioned by way of example and by way of preference: methylcarbonyloxy, ethylcarbonyloxy, n-propylcarbonyloxy, isopropylcarbonyloxy, n-butylcarbonyloxy, isobutylcarbonyloxy and tert-butylcarbonyloxy.

In the context of the invention, alkoxy represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

In the context of the invention, alkylthio represents a straight-chain or branched alkylthio radical having 1 to 6 or 1 to 4 carbon atoms. The following may be mentioned by way of example and by way of preference: methylthio, ethylthio, n-propylthio, isopropylthio, n-butylthio, tert-butylthio, n-pentylthio and n-hexylthio.

In the context of the invention, alkoxycarbonyl represents a straight-chain or branched alkoxy radical having 1 to 6 or 1 to 4 carbon atoms and a carbonyl group attached at the oxygen. Preference is given to a straight-chain or branched alkoxycarbonyl radical having 1 to 4 carbon atoms in the alkoxy group. The following may be mentioned by way of example and by way of preference: methoxycarbonyl, ethoxycarbonyl, n-propoxycarbonyl, isopropoxycarbonyl and tert-butoxycarbonyl.

In the context of the invention, monoalkylamino represents an amino group having a straight-chain or branched alkyl substituent which has 1 to 6 carbon atoms. The following may be mentioned by way of example and by way of preference: methylamino, ethylamino, n-propylamino, isopropylamino and tert-butylamino.

In the context of the invention, dialkylamino represents an amino group having two identical or different straight-chain or branched alkyl substituents having 1 to 6 carbon atoms each. The following may be mentioned by way of example and by way of preference: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

In the context of the invention, monoalkylaminocarbonyl represents an amino group which is attached via a carbonyl group and has a straight-chain or branched alkyl substituent having 1 to 6 or 1 to 4 carbon atoms. Preference is given to a monoalkylaminocarbonyl radical having 1 to 4 carbon atoms in the alkyl group. The following may be mentioned by way of example and by way of preference: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

In the context of the invention, dialkylaminocarbonyl represents an amino group which is attached via a carbonyl group and has two identical or different straight-chain or branched alkyl substituents having 1 to 6 or 1 to 4 carbon atoms each. Preference is given to a dialkylaminocarbonyl radical having 1 to 4 carbon atoms each per alkyl group. The following may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methyl-aminocarbonyl, N-tert-butyl-N-methylaminocarbonyl, N-n-pentyl-N-methylaminocarbonyl and N-n-hexyl-N-methylaminocarbonyl.

In the context of the invention, alkylcarbonylamino represents an amino group having a straight-chain or branched alkylcarbonyl substituent which has 1 to 6 or 1 to 4 carbon atoms in the alkyl chain and is attached via the carbonyl group to the nitrogen atom. The following may be mentioned by way of example and by way of preference: methylcarbonylamino, ethylcarbonylamino, propylcarbonylamino, n-butylcarbonylamino, isobutylcarbonylamino and tert-butylcarbonylamino.

In the context of the invention, alkoxycarbonylamino represents an amino group having a straight-chain or branched alkoxycarbonyl substituent which has 1 to 6 or 1 to 4 carbon atoms in the alkyl chain and is attached via the carbonyl group to the nitrogen atom. The following may be mentioned by way of example and by way of preference: methoxycarbonylamino, ethoxycarbonylamino, propoxycarbonylamino, n-butoxycarbonylamino, isobutoxycarbonylamino and tert-butoxycarbonylamino.

In the context of the invention, 5- to 10-membered heteroaryl represents a mono- or optionally bicyclic aromatic heterocycle (heteroaromatic) having a total of 5 to 10 ring atoms which contains up to three identical or different ring heteroatoms from the group consisting of N, O and S and which is attached via a ring carbon atom or optionally via a ring nitrogen atom. The following may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to mono-cyclic 5- or 6-membered heteroaryl radicals having up to three ring heteroatoms from the group consisting of N, O and S such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

In the context of the invention, a 4- to 8-membered heterocycle represents a monocyclic saturated heterocycle having a total of 4 to 8 ring atoms which contains one or two ring heteroatoms from the group consisting of N, O, S, SO and $SO_2$ and which is attached via a ring carbon atom or optionally via a ring nitrogen atom. Preference is given to a 5- to 7-membered heterocycle having one or two ring heteroatoms from the group consisting of N, O and S, particularly preferably a 5- or 6-membered heterocycle having one or two ring heteroatoms from the group consisting of N and O. The following may be mentioned by way of example: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl and hexahydro-1,4-diazepinyl. Preference is given to pyrrolidinyl, tetrahydrofuranyl, piperidinyl, piperazinyl, tetrahydropyranyl and morpholinyl.

In the context of the invention, halogen includes fluorine, chlorine, bromine and iodine. Preference is given to chlorine or fluorine.

If radicals in the compounds according to the invention are substituted, the radicals may, unless otherwise specified, be substituted one or more times. In the context of the present invention, for all the radicals which occur more than once, the meaning thereof is independent of each other. Substitution by one, two or three identical or different substituents is preferred. Substitution by one substituent is very particularly preferred.

In the context of the present invention, preference is given to compounds of the formula (I) in which
A represents $CR^3$ or N,
  where
    $R^3$ represents hydrogen,
D represents $CR^4$ or N,
  where
    $R^4$ represents hydrogen,
E represents $CR^5$ or N,
  where
    $R^5$ represents hydrogen,
G represents $CR^6$ or N,
  where
    $R^6$ represents hydrogen,
  with the proviso that at most 2 of the groups A, D, E and G represent N,
$R^1$ represents cyclopentyl, cyclohexyl or cycloheptyl,
  where cyclopentyl, cyclohexyl or cycloheptyl may be substituted by 1 or 2 substituents independently of one another selected from the group consisting of fluorine and methyl,
$R^2$ represents a group of the formula

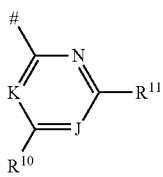

where
# represents the point of attachment to the heterobicycle,
K represents CH or N,
J represents $CR^{12}$, N or $N^+$—$O^-$,
  in which
    $R^{12}$ represents halogen, nitro, cyano, —$R^7$, —C(=O)—$R^7$, —C(=O)—$OR^7$, —C(=O)—$NR^7R^8$, —O—(C=O)$_n$—$R^7$, —O—C(=O)—$OR^7$, —O—C(=O)—$NR^7R^8$, —S(O)$_p$—$R^7$, —$SO_2$—$OR^7$, —$SO_2$—$NR^7R^8$, —$NR^7$—(C=O)$_n$—$R^8$, —$NR^7$—$SO_2$—$R^8$, —$NR^7$—C(=O)—$OR^8$, —$NR^9$—C(=O)—$NR^7R^8$ or —$NR^9$—$SO_2$—$NR^7R^8$,
    in which
      n represents the number 0 or 1,
      P represents the number 0 or 2,
      $R^7$, $R^8$ and $R^9$ each independently of one another represent hydrogen, ($C_1$-$C_6$)-alkyl, ($C_2$-$C_6$)-alkenyl, ($C_3$-$C_7$)-cycloalkyl, ($C_3$-$C_7$)-cycloalkenyl, phenyl, 5- to 7-membered heterocyclyl or 5- or 6-membered heteroaryl,
        in which $R^7$, $R^8$ and $R^9$ for their part may be substituted by 1 to 3 substituents independently of one another selected from the group consisting of fluorine, chlorine, cyano, trifluoromethyl, ($C_1$-$C_4$)-alkyl, hydroxyl, trifluoromethoxy, ($C_1$-$C_4$)-alkoxy, oxo, amino, mono-($C_1$-$C_4$)-alkylamino and di-($C_1$-$C_4$)-alkylamino,
      or
      $R^7$ and $R^8$ together with the radical to which the two are attached form a 5- to 7-membered heterocycle,
      or
      $R^7$ and $R^9$ together with the radical to which the two are attached form a 5- to 7-membered heterocycle,
and N-oxides, salts, solvates, salts of N-oxides and solvates of N-oxides or salts thereof.

In the context of the present invention, particular preference is given to compounds of the formula (I) in which
A represents N,
D represents $CR^4$,
  where
    $R^4$ represents hydrogen,
E represents $CR^5$,
  where
    $R^5$ represents hydrogen,
G represents $CR^6$,
  where
    $R^6$ represents hydrogen,
$R^1$ represents cyclohexyl or cycloheptyl,
$R^2$ represents a group of the formula

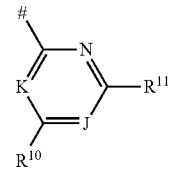

where
# represents the point of attachment to the heterobicycle,
K represents N,
J represents $CR^{12}$ or N,
  in which
    $R^{12}$ represents hydrogen, —$R^7$, —$NR^7$—(C=O)$_n$—$R^8$, —$NR^7$—C(=O)—$OR^8$ or pyridyl,
    in which
      n represents the number 1,
      $R^7$ represents hydrogen, trifluoromethyl or ($C_1$-$C_4$)-alkyl,
        in which ($C_1$-$C_4$)-alkyl for its part may be substituted by a substituent selected from the group consisting of fluorine, trifluoromethyl, hydroxyl and methoxy,
      $R^8$ represents ($C_1$-$C_4$)-alkyl or ($C_3$-$C_7$)-cycloalkyl,
        in which ($C_1$-$C_4$)-alkyl and ($C_3$-$C_7$)-cycloalkyl for their part may be substituted by a substituent selected from the group consisting of fluorine, trifluoromethyl, ($C_1$-$C_4$)-alkyl, hydroxyl, methoxy and
      or
      $R^7$ and $R^8$ together with the radical to which the two are attached form a 5- to 7-membered heterocycle,
and N-oxides, salts, solvates, salts of N-oxides and solvates of N-oxides or salts thereof.

Independently of the respective given combination of the radicals, the specific radical definitions given in the respective combinations or preferred combinations of radicals are also replaced by any radical definitions of other combinations.

Particular preference is given to combinations of two or more of the preferred ranges mentioned above.

The compounds of the formula (I) according to the invention can be prepared by reacting a compound of the formula (II)

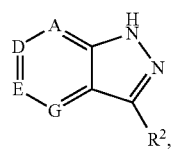
(II)

in which A, D, E, G and $R^2$ each have the meanings given above
in an inert solvent in the presence of a suitable base with a compound of the formula (III)

(III)

in which $R^1$ has the meaning given above
and
$X^1$ represents a suitable leaving group, such as tosylate, mesylate or halogen, in particular bromine,
modifying the resulting compound of the invention, where appropriate, within the scope, given above, of the meanings of the individual substituents and radicals using processes customary in the literature
and converting the resulting compounds of the invention, where appropriate, with the appropriate (i) solvents and/or (ii) acids or bases into their solvates, salts and/or solvates of the salts.

Inert solvents for the process step (II)+(III)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulfoxide, N,N-dimethylformamide (DMF), N,N'-dimethylpropyleneurea (DMPU) or N-methylpyrrolidone (NMP). It is also possible to use mixtures of the solvents mentioned above. Preference is given to using dimethylformamide.

Suitable bases for the process step (II)+(III)→(I) are the customary inorganic or organic bases. These preferably include alkali metal hydroxides such as, for example, lithium hydroxide, sodium hydroxide or potassium hydroxide, alkali metal or alkaline earth metal carbonates such as lithium carbonate, sodium carbonate, potassium carbonate or cesium carbonate, alkali metal alkoxides such as sodium methoxide or potassium methoxide, sodium ethoxide or potassium ethoxide or lithium tert-butoxide, sodium tert-butoxide or potassium tert-butoxide, alkali metal hydrides such as sodium hydride or potassium hydride, amides such as sodium amide, lithium bis(trimethylsilyl)-amide or potassium bis(trimethylsilyl)amide or lithium diisopropylamide, or organic amines such as N,N-diisopropylethylamine, 1,5-diazabicyclo[4.3.0]non-5-ene (DBN) and 1,8-diazabicyclo[5.4.0]undec-7-ene (DBU). Preference is given to using cesium carbonate and sodium hydride.

Here, the base is employed in an amount of from 1 to 5 mol, preferably in an amount of from 1 to 2.5 mol, per mole of the compound of the formula (II). The reaction is generally carried out in a temperature range of from −10° C. to +100° C., preferably at from +0° C. to +30° C. The reaction can be carried out at atmospheric, elevated or reduced pressure (for example at from 0.5 to 5 bar), if appropriate in a microwave. The reaction is generally carried out at atmospheric pressure.

The compounds of the formula (II) are known from the literature or can be prepared analogously to processes known from the literature starting with compounds which are commercially available or have been described in the literature [cf., for example, WO 03/095451 and WO 03/097063].

The compounds of the formula (III) are commercially available, known from the literature or can be prepared analogously to processes known from the literature.

The preparation of the compounds according to the invention can be illustrated in an exemplary manner by the synthesis schemes below:

Scheme 1

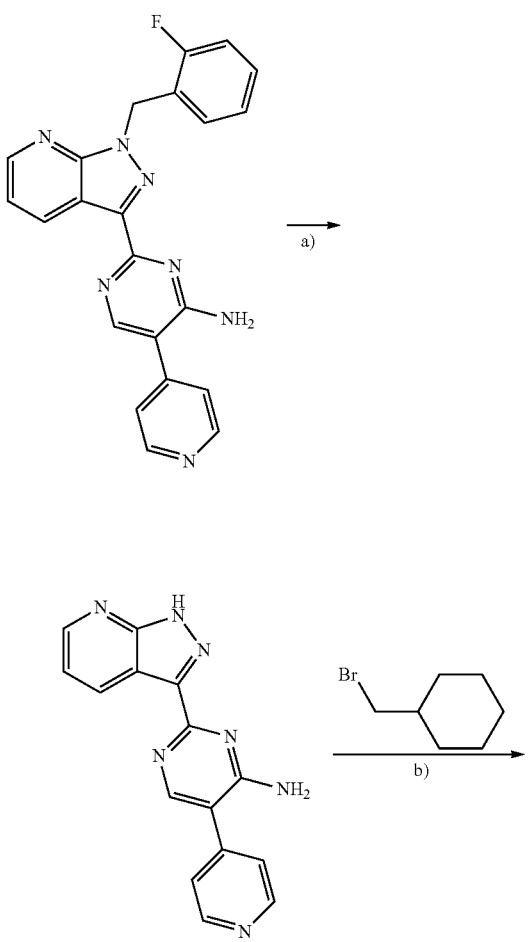

-continued

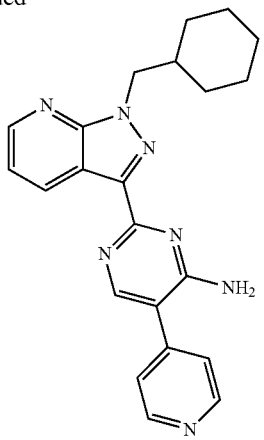

[a) sodium, NH$_3$, NH$_4$Cl; b) CsCO$_3$, DMF]

The compounds according to the invention have valuable pharmacological properties and can be used for the prevention and treatment of disorders in humans and animals. The compounds according to the invention offer a further treatment alternative and enlarge pharmacy.

The compounds according to the invention lead to vasorelaxation, to an inhibition of platelet aggregation and to a reduction in blood pressure, and also to an increase in coronary blood flow. These effects are mediated by direct stimulation of soluble guanylate cyclase and an increase in intracellular cGMP. Moreover, the compounds according to the invention enhance the effect of substances increasing the cGMP concentration, such as, for example, EDRF (endothelium-derived relaxing factor), NO donors, protoporphyrin IX, arachidonic acid or phenylhydrazine derivatives.

The compounds according to the invention can therefore be employed in medicaments for the treatment of cardiovascular disorders such as, for example, for the treatment of high blood pressure and heart failure, stable and unstable angina pectoris, pulmonary hypertension, peripheral and cardiac vascular disorders, arrhythmias, for the treatment of thromboembolic disorders and ischemias such as myocardial infarction, stroke, transistoric and ischemic attacks, disturbances of peripheral blood flow, reperfusion damage, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, and incontinence, osteoporosis, glaucoma, and gastroparesis.

The compounds according to the invention can additionally be used for the treatment of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system, kidney disorders such as, for example, acute or chronic renal failure, immunological kidney disorders such as kidney transplant rejection, glumerulonephritis, immune complex-induced kidney disorders, glomerulopathies, nephritis, toxic nephropathy and obstructive uropathies.

The compounds according to the invention are furthermore suitable for the treatment of acute and chronic lung diseases, such as respiratory distress syndromes (ALI, ARDS) and chronic obstructive airway disorders (COPD), and also for the treatment of acute and chronic renal failure.

The compounds described in the present invention also represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischemias and craniocerebral trauma. The compounds according to the invention can likewise be employed for controlling states of pain.

In addition, the compounds according to the invention have an anti-inflammatory effect and can therefore be employed as anti-inflammatory agents.

The present invention further relates to the use of the compounds according to the invention for the treatment and/or prevention of disorders, especially of the aforementioned disorders.

The present invention further relates to the compounds according to the invention for use in a method for the treatment and/or prevention of heart failure, angina pectoris, hypertension, pulmonary hypertension, ischemias, vascular disorders, thromboembolic disorders and arteriosclerosis.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prevention of the aforementioned disorders. Mention may be made, by way of example and preferably, of the following active ingredients suitable for combinations:

- organic nitrates and NO donors such as, for example, sodium nitroprusside, nitroglycerin, isosorbide mononitrate, isosorbide dinitrate, molsidomine or SIN-1, and inhaled NO;
- compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
- agents having antithrombotic activity, for example and preferably from the group of platelet aggregation inhibitors, of anticoagulants or of profibrinolytic substances;
- active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
- active ingredients which modify lipid metabolism, for example and preferably from the group of thyroid receptor agonists, cholesterol synthesis inhibitors such as, for example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, for example and preferably, aspirin, clopidogrel, ticlopidin or dipyridamole.

In a preferred embodiment of the invention, the compounds according to the invention are administered in combination with a thrombin inhibitor such as, for example and preferably, ximelagatran, melagatran, bivalirudin or clexane.

In a preferred embodiment of the invention, the compounds according to the invention are administered in combination with a GPIIb/IIIa antagonist such as, for example and preferably, tirofiban or abciximab.

In a preferred embodiment of the invention, the compounds according to the invention are administered in combination with a factor Xa inhibitor such as, for example and preferably, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist such as, for example and preferably, coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics.

In a preferred embodiment of the invention, the compounds according to the invention are administered in combination with a calcium antagonist such as, for example and preferably, nifedipine, amlodipine, verapamil or diltiazem.

In a preferred embodiment of the invention, the compounds according to the invention are administered in combination with an alpha-1-receptor blocker such as, for example and preferably, prazosin.

In a preferred embodiment of the invention, the compounds according to the invention are administered in combination with a beta-receptor blocker such as, for example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, for example and preferably, losartan, candesartan, valsartan, telmisartan or embursatan.

In a preferred embodiment of the invention, the compounds according to the invention are administered in combination with an ACE inhibitor such as, for example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, for example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic such as, for example and preferably, furosemide.

Agents which modify lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and of lipoprotein (a) antagonists.

In a preferred embodiment of the invention, the compounds according to the invention are administered in combination with a CETP inhibitor such as, for example and preferably, torcetrapib (CP-529 414), JTT-705 or CETP vaccine (Avant).

In a preferred embodiment of the invention, the compounds according to the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as, for example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as, for example and preferably, BMS-188494 or TAK-475.

In a preferred embodiment of the invention, the compounds according to the invention are administered in combination with an ACAT inhibitor such as, for example and preferably, avasimibe, melinamide, pactimibe, eflucimibe or SMP-797.

In a preferred embodiment of the invention, the compounds according to the invention are administered in combination with an MTP inhibitor such as, for example and preferably, implitapide, BMS-201038, R-103757 or JTT-130.

In a preferred embodiment of the invention, the compounds according to the invention are administered in combination with a PPAR-gamma agonist such as, for example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, for example and preferably, ezetimibe, tiqueside or pamaqueside.

In a preferred embodiment of the invention, the compounds according to the invention are administered in combination with a lipase inhibitor such as, for example and preferably, orlistat.

In a preferred embodiment of the invention, the compounds according to the invention are administered in combination with a polymeric bile acid adsorbent such as, for example and preferably, cholestyramine, colestipol, colesolvam, CholestaGel or colestimide.

In a preferred embodiment of the invention, the compounds according to the invention are administered in combination with a bile acid reabsorption inhibitor such as, for example and preferably, ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein (a) antagonist such as, for example and preferably, gemcabene calcium (CI-1027) or nicotinic acid.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations

| | |
|---|---|
| aq. | aqueous solution |
| br.s | broad singlet (in NMR) |
| DCC | N,N'-dicyclohexylcarbodiimide |
| DMF | dimethylformamide |
| DMSO | dimethyl sulfoxide |
| eq. | equivalent(s) |
| ESI | electrospray ionization (in MS) |
| Et | ethyl |
| h | hour(s) |
| HOAc | acetic acid |
| HOBt | 1-hydroxy-1H-benzotriazole × $H_2O$ |
| HPLC | high-pressure, high-performance liquid chromatography |
| iPr | isopropyl |
| LC/MS | liquid chromatography-coupled mass spectroscopy |
| LDA | lithium diisopropylamide |
| min | minute(s) |
| MS | mass spectrometry |
| NMR | nuclear magnetic resonance spectroscopy |
| RT | room temperature |
| $R_t$ | retention time (in HPLC) |
| THF | tetrahydrofuran |
| UV | ultraviolet spectrometry |
| v/v | ratio by volume (of a solution) |

LC/MS and HPLC Methods:

Method 1 (LC/MS):

Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 2 (LC/MS):

MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3 (LC/MS):

Instrument: Micromass Platform LCZ with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 4 (Preparative HPLC):

Column: Kromasil 100 C 18, 5 μm, 250 mm×20 mm; mobile phase A: 0.2% trifluoroacetic acid in water, mobile phase B: acetonitrile; A:B 60:40 isocratic; flow rate: 25 ml/min; injection volume 500 μl, temperature 30° C.

Method 5 (Preparative HPLC):

Column: Grom-Sil 120 ODS-4HE, 10 μm, 250 mm×30 mm; mobile phase A: 0.1% formic acid in water, mobile phase B: acetonitrile; flow rate: 50 ml/min; gradient: 0-3 min 10% B, 3-27 min 10%→95% B, 27-34 min 95% B, 34-38 min 10% B.

Starting Material

Example 1A

Methyl[4,6-diamino-2-(1H-pyrazolo[3,4-b]pyridin-3-yl)pyrimidin-5-yl]carbamate

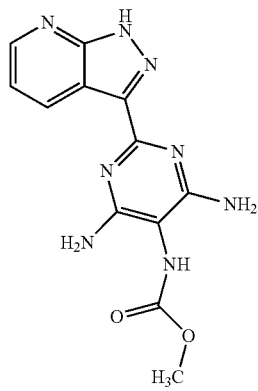

With dry-ice cooling, 540 ml of ammonia were condensed in a 1 l flask. A little at a time, 8.1 g (352.6 mmol) of sodium were added at about −50° C., and the mixture was stirred at −40° C. for 0.5 h. 36.0 g (88.1 mmol) of methyl {4,6-diamino-2-[1-(2-fluorobenzyl)-1H-pyrazolo[3,4-b]pyridin-3-yl]pyrimidin-5-yl}carbamate (preparation: see WO 03/095451, Example 5) were then added. The mixture was stirred at the same temperature for 5 h, 28.3 g (528.9 mmol) of ammonium chloride were then added and the mixture was stirred at −40° C. for a further 0.5 h. Cooling was then removed, and the mixture was allowed to stand without stirring overnight to let the ammonia evaporate. 750 ml of water were added to the residue. The mixture was stirred for 0.5 h, and the solid was then filtered off with suction and dried under reduced pressure.

This crude product (34 g) was dissolved in a mixture of 200 ml of methanol, 50 ml of THF and 50 ml of water. The solution was adjusted to pH 2 using trifluoroacetic acid and separated in portions by HPLC (Method 4). This gave a total of 11.3 g of recovered starting material and 17.8 g (51% of theory) of a product-containing fraction (purity 76% (LC-MS)).

1 g of this fraction was re-purified by preparative HPLC (Method 5). This gave 116 mg of product of good purity (about 8% of theory).

$^1$H-NMR (400 MHz, DMSO-$d_6$): δ=14.8 (br.s, 1H), 13.3-12.5 (br.s, 2 H), 8.91 (d, J=8.1 Hz, 1H), 8.71 (d, J=4.7 Hz, 1H), 8.34 (s, 1H), 7.46 (dd, J=8.1, 4.7 Hz, 1H), 3.66 (s, 3H).

LC-MS (Method 3): $R_t$=2.11 Min.; MS (ESIpos): m/z=301 [M+H]$^+$.

Exemplary Embodiments

Example 1

Methyl[4,6-diamino-2-(1-cyclohexylmethyl-1H-pyrazolo[3,4-b]pyridin-3-yl)pyrimidin-5-yl]carbamate

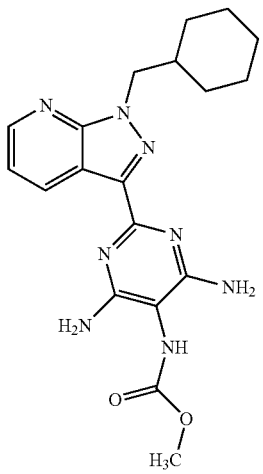

330 mg (1.1 mmol) of the compound of Example 1A and 212 mg (1.2 mmol) of bromomethylcyclohexane were initially charged in 5 ml of dimethylformamide, 389 mg (1.2 mmol) of cesium carbonate were added and the resulting mixture was stirred at RT overnight. 0.5 ml of 1N hydrochloric acid was added, and the entire solution was separated by HPLC (Method 5). The appropriate fractions were freed from volatile components on a rotary evaporator, and the residue was dried under high vacuum. This gave 60 mg (19% of theory) of the target compound.

$^1$H-NMR (500 MHz, DMSO-$d_6$): δ=9.03 (d, 1H), 8.55 (d, 1H), 8.04 (s, 1H), 7.28 (dd, 1H), 6.16 (br. s, 4H), 4.35 (d, 2H), 3.63 (s, 3H), 2.00 (m, 1H), 1.69-1.46 (m, 5H), 1.19-1.10 (m, 3H), 1.08-0.98 (m, 2H).

LC-MS (Method 1): $R_t$=1.61 Min.; MS (ESIpos): m/z=397 [M+H]$^+$.

Example 2

Methyl[4,6-diamino-2-(1-cycloheptylmethyl-1H-pyrazolo[3,4-b]pyridin-3-yl)pyrimidin-5-yl]-carbamate

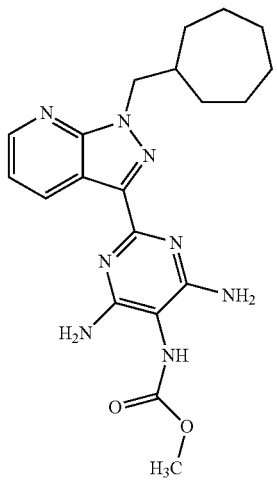

300 mg (1.0 mmol) of the compound of Example 1A and 224 mg (1.1 mmol) of cycloheptylmethyl methansulfonate (preparation: see *J. Med. Chem.* 2000, 43(26), 5017-5029) were initially charged in 5 ml of dimethylformamide, 354 mg (1.1 mmol) of cesium carbonate were added and the resulting mixture was stirred at RT overnight. 0.5 ml of 1N hydrochloric acid was added, and the entire solution was separated by HPLC (Method 5). The appropriate fractions were concentrated on a rotary evaporator, and the residue was dried under high vacuum. This gave 2.8 mg (0.7% of theory) of the target compound.

$^1$H-NMR (400 MHz, CDCl$_3$): δ=8.82 (d, 1H), 8.55 (d, 1H), 8.14 (br. s, 1H), 7.19 (dd, 1H), 6.0 (br. S, 1H), 5.35-5.05 (br. s, 3H), 4.44 (d, 2H), 3.79 (s, 3H), 2.42 (m, 1H), 1.69-1.21 (m, 12H).

LC-MS (Method 1): $R_t$=1.80 Min.; MS (ESIpos): m/z=411 [M+H]$^+$.

Example 3

Methyl N-[4,6-diamino-2-(1-cyclohexylmethyl-1H-pyrazolo[3,4-b]pyridin-3-yl)pyrimidin-5-yl]-N-methylcarbamate

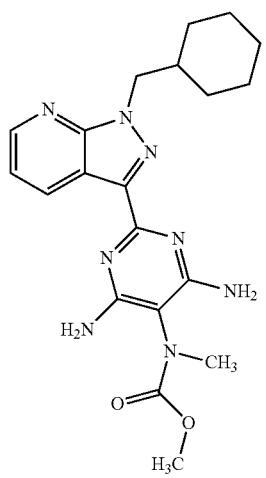

24 mg (61 μmol) of the compound of Example 1 were initially charged in 1 ml of dimethylformamide, and about 2.7 mg (70 μmol) of sodium hydride (60% in mineral oil) were added. The resulting mixture was stirred at RT for 10 min, 6 μl (9 μmol) of iodomethane were then added and the reaction was stirred overnight. 0.5 ml of 1N hydrochloric acid was added, and the entire mixture was separated by HPLC (Method 5). The appropriate fractions were concentrated on a rotary evaporator, and the residue was dried under high vacuum. This gave 8 mg (32% of theory) of the target compound.

$^1$H-NMR (500 MHz, CDCl$_3$): δ=8.88 (dd, 1H), 8.55 (dd, 1H), 7.20 (dd, 1H), 4.84 (br s, 4H), 4.49 (d, 2H), 3.70 (br s, 3H), 3.20 (s, 3H), 2.20 (m, 1H), 1.69-1.60 (m, 3H), 1.56-1.51 (m, 2H), 1.22-1.03 (m, 5H).

LC-MS (Method 2): $R_t$=1.62 Min.; MS (ESIpos): m/z=411 [M+H]$^+$.

Example 4

2-[1-(Cyclohexylmethyl)-1H-pyrazolo[3,4-b]pyridin-3-yl]-5-(pyridin-4-yl)pyrimidine-4-amine

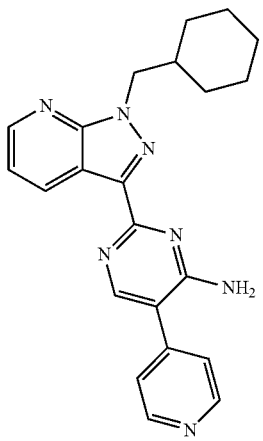

200 mg (0.691 mmol) of 2-(1H-pyrazolo[3,4-b]pyridin-3-yl)-5-(pyridin-4-yl)pyrimidine-4-amine (preparation: see WO 03/097063, Example 35A) were dissolved in 5 ml of DMF, and 248 mg (0.760 mmol) of cesium carbonate and 136 mg (0.760 mmol) of cyclohexylmethyl bromide were added. The mixture was stirred at RT overnight. Water was added, and the mixture was extracted three times with dichloromethane. The combined organic phases were washed with saturated aqueous sodium chloride solution, dried over sodium sulfate and concentrated on a rotary evaporator. The residue was fractionated by preparative HPLC (Method 5). The product-containing fractions were combined and concentrated on a rotary evaporator, and the residue was dried under high vacuum. This gave 29 mg (11% of theory) of the target compound.

$^1$H-NMR (500 MHz, CDCl$_3$): δ=1.08-1.25 (m, 5H), 1.56-1.71 (m, 5H), 2.20-2.28 (m, 1H), 4.51 (d, 2H), 5.33 (s br, 2H), 7.25 (dd, 1H), 7.46 (d, 2H), 8.40 (s, 1H), 8.59 (d, 1H), 8.77 (s br, 2H), 8.94 (d, 1H).

LC-MS (Method 1): R$_t$=1.84 Min.; MS (ESIpos): m/z=386 [M+H]$^+$.

Example 5

2-[1-(Cycloheptylmethyl)-1H-pyrazolo[3,4-b]pyridin-3-yl]-5-(pyridin-4-yl)pyrimidine-4-amine

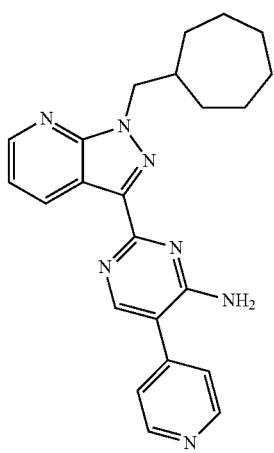

200 mg (0.691 mmol) of 2-(1H-pyrazolo[3,4-b]pyridin-3-yl)-5-(pyridin-4-yl)pyrimidine-4-amine (preparation: see WO 03/097063, Example 35A) were dissolved in 4 ml of DMF, and 451 mg (1.383 mmol) of cesium carbonate and 288 mg (1.383 mmol) of cycloheptylmethyl methanesulfonate (preparation: see WO 96/05193, p. 147) were added. The mixture was stirred at RT overnight. Water was added, and the mixture was extracted three times with dichloromethane. The combined organic phases were washed with saturated aqueous sodium chloride solution, dried over sodium sulfate and concentrated on a rotary evaporator. The residue was fractionated by preparative HPLC (Method 5). The product-containing fractions were combined and concentrated on a rotary evaporator. The residue was dried under high vacuum. This gave 45 mg (16% of theory) of the target compound.

$^1$H-NMR (500 MHz, DMSO-d$_6$): δ=1.21-1.66 (m, 12H), 2.24-2.34 (m, 1H), 4.40 (d, 2H), 7.17 (s br, 2H), 7.36 (dd, 1H), 7.56 (d, 2H), 8.29 (s, 1H), 8.61 (dd, 1H), 8.68 (d, 2H), 9.01 (dd, 1H).

LC-MS (Method 1): R$_t$=1.97 Min.; MS (ESIpos): m/z=400 [M+H]$^+$.

B. Assessment of the Pharmacological Activity

The pharmacological effect of the compounds according to the invention can be shown in the following assays:

B-1. Vasorelaxant Effect In Vitro

Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): NaCl: 119; KCl: 4.8; CaCl$_2$×2H$_2$O: 1; MgSO$_4$×7H$_2$O: 1.4; KH$_2$PO$_4$: 1.2; NaHCO$_3$: 25; glucose: 10. The force of contraction is detected with Statham UC2 cells, amplified and digitized via A/D converters (DAS-1802 HC, Keithley Instruments, Munich) and recorded in parallel on chart recorders. Contractions are induced by cumulatively adding increasing concentrations of phenylephrine to the bath. After several control cycles, the substance to be investigated is added in each further run in increasing dosage in each case, and the height of the contraction achieved is compared with the height of the contraction reached in the last preceding one. The concentration necessary to reduce the height of the control value by 50% is calculated from this (IC$_{50}$ value). The standard application volume is 5 μl, the proportion of DMSO in the bath solution corresponds to 0.1%.

Representative IC$_{50}$ values for the compounds according to the invention are shown in the table below:

| Example No. | IC$_{50}$ [nM] |
| --- | --- |
| 1 | 870 |
| 5 | 1000 |

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

C. Exemplary Embodiments of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm

Production:

The mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400.20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

I.V. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

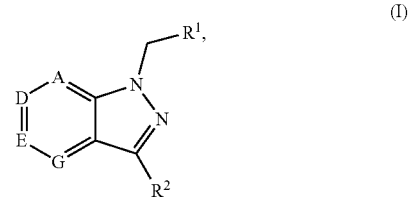

in which
A represents $CR^3$ or N,
where
$R^3$ represents hydrogen,
D represents $CR^4$ or N,
where
$R^4$ represents hydrogen,
E represents $CR^5$ or N,
where
$R^5$ represents hydrogen,
G represents $CR^6$ or N,
where
$R^6$ represents hydrogen,
with the proviso that at most 2 of the groups A, D, E and G represent N,
$R^1$ represents cyclopentyl, cyclohexyl or cycloheptyl,
where cyclopentyl, cyclohexyl or cycloheptyl may be substituted by 1 or 2 substituents independently of one another selected from the group consisting of fluorine and methyl,
$R^2$ represents a group of the formula

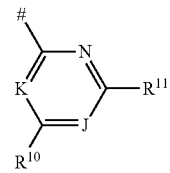

where
# represents the point of attachment to the heterobicycle,
$R^{10}$ and $R^{11}$ independently represent H or $NH_2$,
K represents CH or N,
J represents $CR^{12}$, N or $N^+$—$O^-$,
in which
$R^{12}$ represents halogen, nitro, cyano, —$R^7$, —C(=O)—$R^7$, —C(=O)—$OR^7$, —C(=O)—$NR^7R^8$, —O—(C=O)$_n$—$R^7$, —O—C(=O)—$OR^7$, —O—C(=O)—$NR^7R^8$, —S(O)$_p$—$R^7$, —$SO_2$—$OR^7$, —$SO_2$—$NR^7R^8$, —$NR^7$—(C=O)$_n$—$R^8$, —$NR^7$—$SO_2$—$R^8$, —$NR^7$—C(=O)—$OR^8$, —$NR^9$—C(=O)—$NR^7R^8$ or —$NR^9$—$SO_2$—$NR^7R^8$,
in which
n represents the number 0 or 1,
p represents the number 0 or 2,
$R^7$, $R^8$ and $R^9$ each independently of one another represent hydrogen, ($C_1$-$C_6$)-alkyl, ($C_2$-$C_6$)-alkenyl, ($C_3$-$C_7$)-cycloalkyl, ($C_3$-$C_7$)-cycloalkenyl, phenyl, 5- to 7-membered heterocyclyl or 5- or 6-membered heteroaryl, in which $R^7$, $R^8$ and $R^9$ for their part may be substituted by 1 to 3 substituents independently of one another selected from the group consisting of fluorine, chlorine, cyano, trifluoromethyl, $(C_1-C_4)$-alkyl, hydroxyl, trifluoromethoxy, $(C_1-C_4)$-alkoxy, oxo, amino, mono-$(C_1-C_4)$-alkylamino and di-$(C_1-C_4)$-alkylamino, or $R^7$ and $R^8$ together with the radical to which the two are attached form a 5- to 7-membered heterocycle, or $R^7$ and $R^9$ together with the radical to which the two are attached form a 5- to 7-membered heterocycle, or an N-oxide, salt, or salt of an N-oxide thereof.

2. The compound of the formula (I) of claim 1 in which
A represents N,
D represents $CR^4$,
  where
  $R^4$ represents hydrogen,
E represents $CR^5$,
  where
  $R^5$ represents hydrogen,
G represents $CR^6$,
  where
  $R^6$ represents hydrogen,
$R^1$ represents cyclohexyl or cycloheptyl,
$R^2$ represents a group of the formula

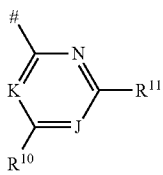

where
# represents the point of attachment to the heterobicycle,
$R^{10}$ and $R^{11}$ independently represent H or $NH_2$,
K represents N,
J represents $CR^{12}$ or N,
  in which
    $R^{12}$ represents hydrogen, —$R^7$, —$NR^7$—(C=O)$_n$—$R^8$, —$NR^7$—C(=O)—$OR^8$ or pyridyl,
    in which
      n represents the number 1,
      $R^7$ represents hydrogen, trifluoromethyl or $(C_1-C_4)$-alkyl, in which $(C_1-C_4)$-alkyl for its part may be substituted by a substituent selected from the group consisting of fluorine, trifluoromethyl, hydroxyl and methoxy,
    $R^8$ represents $(C_1-C_4)$-alkyl or $(C_3-C_7)$-cycloalkyl, in which $(C_1-C_4)$-alkyl and $(C_3-C_7)$-cycloalkyl for their part may be substituted by a substituent selected from the group consisting of fluorine, trifluoromethyl, $(C_1-C_4)$-alkyl, hydroxyl, methoxy and oxo, or $R^7$ and $R^8$ together with the radical to which the two are attached form a 5- to 7-membered heterocycle, or an N-oxide, salt, or salt of an N-oxide thereof.

3. A process for preparing a compound of the formula (I) as defined in claim 1, characterized in that a compound of formula (II)

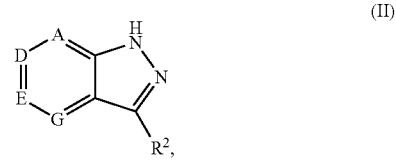

in which A, D, E, G and $R^2$ each have the meanings given in claim 1 is reacted in an inert solvent in the presence of a suitable base with a compound of the formula (III)

in which $R^1$ has the meaning given in claim 2
and
$X^1$ represents a suitable leaving group, such as tosylate, mesylate or halogen, in particular bromine,
and the resulting compounds of formula (I) is, optionally, converted with an appropriate (i) solvent and/or (ii) base or acids into a salt thereof.

4. A pharmaceutical composition comprising a compound of the formula (I) as defined in claim 1 and an inert, non-toxic, pharmaceutically suitable excipient.

5. The pharmaceutical composition of claim 4, further comprising an active ingredient selected from the group consisting of organic nitrates, NO donors, cGMP-PDE inhibitors, agents having antithrombotic activity, agents lowering blood pressure, and agents altering lipid metabolism.

* * * * *